United States Patent [19]

Kroll et al.

[11] Patent Number: 4,890,630
[45] Date of Patent: Jan. 2, 1990

[54] BIO-ELECTRIC NOISE CANCELLATION SYSTEM

[75] Inventors: Mark W. Kroll; Kenneth M. Olson, both of Minnetonka; Patrick S. Flynn, West St. Paul, all of Minn.

[73] Assignee: Cherne Medical, Inc., Minneapolis, Minn.

[21] Appl. No.: 299,086

[22] Filed: Jan. 23, 1989

[51] Int. Cl.$^4$ .............................................. A61B 5/04
[52] U.S. Cl. .................................. 128/901; 128/905; 128/696; 128/902
[58] Field of Search ........... 128/696, 905, 901, 419 R, 128/902, 697, 700

[56] References Cited

U.S. PATENT DOCUMENTS

| | | | |
|---|---|---|---|
| 3,534,282 | 10/1970 | Day ........................................ | 128/696 |
| 4,200,109 | 4/1980 | McMorrow, Jr. .................. | 128/696 |
| 4,243,044 | 1/1981 | Blancke ............................... | 128/696 |
| 4,360,784 | 11/1982 | Bartlett ................................. | 128/908 |
| 4,630,204 | 12/1986 | Mortava ............................... | 128/901 |

Primary Examiner—Francis Jaworski
Assistant Examiner—George Manuel
Attorney, Agent, or Firm—Anthony G. Eggink

[57] ABSTRACT

A device and method are provided for bio-electric monitoring apparatus to cancel bio-electric noise on the body of a patient. The device comprises a plurality of monitoring electrodes for reception of bio-electric signals from the body, each monitoring electrode having a conductive lead and a surrounding shield. The device further has a driving electrode for transmission of a correction voltage to the body. The driving electrode has a conductive lead and a surrounding shield. The device has a signal averager with an input and an output. The monitoring electrode leads are connected to the input of the signal averager. An amplifier is connected to the output of the signal averager which has its output connected to the driving electrode lead to provide the correction voltage. The shield around the driving electrode lead is conductively connected to the output of the amplifier. The method comprises the steps of obtaining bio-electric signals from a plurality of locations on the body and transmitting the signals via shielded leads. The signals are averaged to provide a signal that is amplified by a predetermined large, negative factor to provide a correction signal, which is then driven to the body via a shielded lead. A conductive link is established between the driving lead shield and the correction signal.

20 Claims, 3 Drawing Sheets

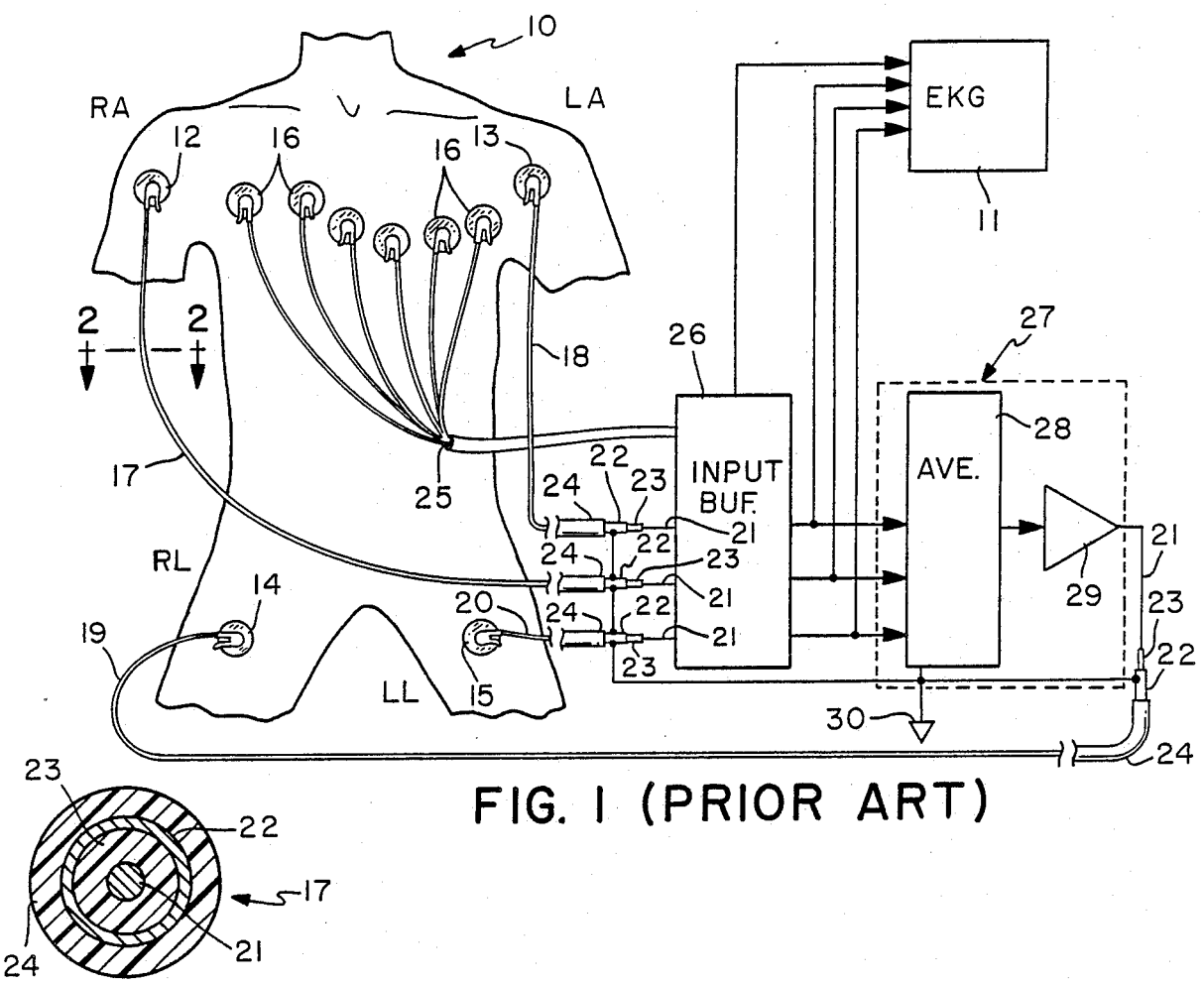
FIG. 1 (PRIOR ART)
FIG. 2
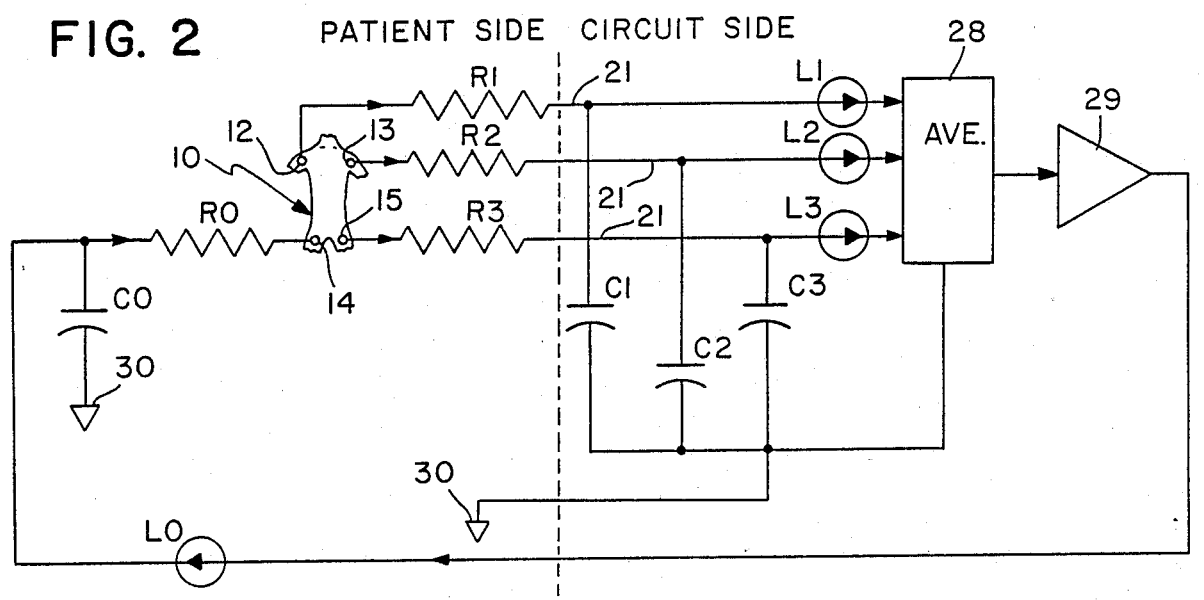
FIG. 3

BIO-ELECTRIC NOISE CANCELLATION SYSTEM

BACKGROUND OF THE INVENTION

This invention relates to medical diagnostic systems. More particularly, this invention relates to an electronic negative feedback, noise cancellation device and method. The device and method of this invention are for use with electronic medical diagnostic apparatus which require a conductive reference connection to the body of a patient.

Bio-electric signals or voltages are obtained from patient bodies for various purposes, foremost to provide information to diagnostitians. Examples of electromedical diagnostic techniques include the electrocardiogram (EKG), electroencephalogram (EEG), and electromyogram (EMG).

Medical diagnostic apparatus which measure bioelectric signals typically require a connection between the patient's body and a reference voltage. In the past, this connection was commonly established by grounding the human body to the circuitry of the diagnostic apparatus. The physical connection was usually provided by an electrode adhesively applied to the skin and which has a conductive lead or cable which is connected to the apparatus. In the case of an EKG connection, for example, the patient's body, usually the right leg, was connected directly to the EKG equipment ground. However, this configuration provided a potential current sink in the case of equipment malfunction or patient contact with an outside current source. Because of patient safety concerns, the practice of using a direct connection to ground is not desirable and no longer used.

One accepted EKG practice is to connect a current limiting device, such as a large resistor, between the patient and the connection to ground. This provides the necessary safety factor, but will also add noise to the system. Noise, however, can interfere with the diagnostic analysis of cardiac activity by medical personnel or by electromedical apparatus. Another accepted EKG practice is to connect the patient's right leg to a reference voltage of an isolated or floating-input amplifier. The bio-electric signals from the patient body are then transmitted to the EKG apparatus for analysis via a nonconductive signal path. Examples of such nonconductive signal paths include optical fibers or transformer isolation couplers. Although this practice adds less system noise than the connection of a resistor current limiter, an appreciable level of noise or common mode voltage remains on the body due to environmental interference and which also can interfere with the accurate measurement of sensitive low-level bio-electric signals.

Two major classifications of noise exist with respect to bio-electric signals. The first, random noise, is a relatively uniform disturbance which is present throughout an entire signal. Types of random noise include Johnson noise and shot noise. Johnson noise or thermal noise is produced by thermal agitation of charges in a conductor and is characterized by a uniform energy versus frequency distribution. Johnson noise is random in that it contains no periodic components and its future value is completely unpredictable. Shot noise is exhibited by fluctuations of current output average value resulting from random emissions of electrons. Johnson and shot noise are both white, in that they have a constant energy per unit band width that is independent of the central frequency of the band. The second noise classification, periodic noise, is caused by outside interference sources such as building wire and fluorescent lights. It is not a truly random noise in that the frequencies exhibited are multiples of the basic line frequencies (i.e., 60, 120, and 180 Hz in the U.S.). Cancellation of this externally caused periodic noise is the subject of this invention.

A current EKG connection practice, which has advantages over each of the previously described methods, is the application of a negative, "noise cancelling" feedback or correction voltage to the patient's body. This practice involves sensing voltages from the body via a plurality of monitoring electrodes. The multiple voltages obtained are processed to yield an average voltage which represents, and is indicative of, the noise level on the body. The average "noise-level" voltage is then amplified by a negative amplification factor and transmitted back to the body, typically at the right leg, by an additional electrode. The negative feedback or correction voltage forces the body potential toward zero. When the patient's body attains zero voltage, the amplifier no longer drives an appreciable current and a state of equilibrium is achieved at which noise on the body is cancelled. When used in conjunction with either of the previously described current limitation or current isolation techniques, the negative feedback system provides the dual advantages of patient safety and noise cancellation in use with the EKG apparatus. Because the negative feedback is transmitted to the right leg of the human body, this practice is commonly referred to as "right leg driving."

However, a factor that significantly limits the performance of the negative feedback system is that feedback time delays destabilize the EKG or other monitoring system. The time delays are inherent in the circuitry of these prior art feedback devices due to resistance/capacitance effects of the circuit topology, which will be further described below. The time delays result in overcompensation and cause the monitoring system to oscillate and destabilize.

Prior attempts to reduce oscillations and improve stability in negative feedback systems included decreasing the sensitivity of the system. The lowering of amplification or gain of the feedback system reduces sensitivity, so that a given noise-level voltage (error voltage) will not generate as large a feedback voltage (correction voltage) for output. The major disadvantage of this technique, however, is the loss of accurate control of the parameter that is sought to be controlled. The amount of noise remaining on the body as a result of limiting the sensitivity of the negative feedback may still constitute an appreciable level when compared to the low voltage biomedical signals that may be desired to be monitored. For example, approximately 100 microvolts (uV) of 60 Hz noise may remain on the body which is a relatively large fraction of the total EKG signal, whose peak amplitude may only be 1 or 2 millivolts (mV). Although such noise levels have been reluctantly tolerated by diagnostitians using conventional EKG apparatus, modern electrocardiographic signal analysis systems measure increasingly lower level signal characteristics which are masked by these noise levels.

Although right leg driving systems such as those previously described are known in the art, insofar as is known, no solution to the problem of minimizing feedback delay without loss of sensitivity has been proposed or developed. Accordingly, it is an object of this invention to provide a method and apparatus which minimizes the time delay of a medical, negative feedback, right leg driving system without compromising patient safety or diagnostic sensitivity.

SUMMARY OF THE INVENTION

This invention provides a method and device for cancelling noise voltages on the body of a patient. The device is a negative feedback, noise cancelling system for an electro-medical diagnostic apparatus used to monitor a patient. The device comprises a plurality of monitoring electrodes for reception of bio-electric signals from the patient. Each monitoring electrode has a conductive lead which is shielded. A driving electrode, which also has a shielded conductive lead, is provided for transmission of a correction voltage to the patient. Signal averaging means is provided to receive signals from the monitoring electrodes and to provide an output average signal. A driver amplifier receives the output average signal at its input and outputs the correction voltage to the driving electrode lead. A conductive connection links the driver amplifier output and the shield around the driving electrode lead and preferably the shields around the monitoring electrode leads.

The device further comprises a current limiter connected between the driver amplifier output and the driving electrode lead at a point after the connection of the lead shields. A first capacitor is connected in parallel with the current limiter. A second capacitor is connected in series with the communicative link between the driver amplifier output and the lead shields.

The method of reducing feedback delay in a medical, negative feedback system comprises the steps of obtaining bio-electric signals from a plurality of locations on the patient body and transmitting the signals via shielded leads. The signals are averaged to provide a signal that is amplified by a predetermined large, negative factor to provide a correction or feedback signal. The correction signal is driven to the body via a shielded lead. Importantly, the process provides a conductive link between the driving lead shield and the correction signal.

These and other benefits of this invention will become clear from the following description by reference to the drawings.

BRIEF DESCRIPTION OF THE DRAWINGS

FIG. 1 is a diagram generally showing the basic connections of an EKG apparatus to the patient's body and utilizing a prior art negative feedback system;

FIG. 2 is a cross-sectional view of a standard medical electrode cable;

FIG. 3 is a schematic circuit representation of the patient body connections to the prior art negative feedback system shown in FIG. 1;

DESCRIPTION OF THE PREFERRED EMBODIMENT

Figure 4:
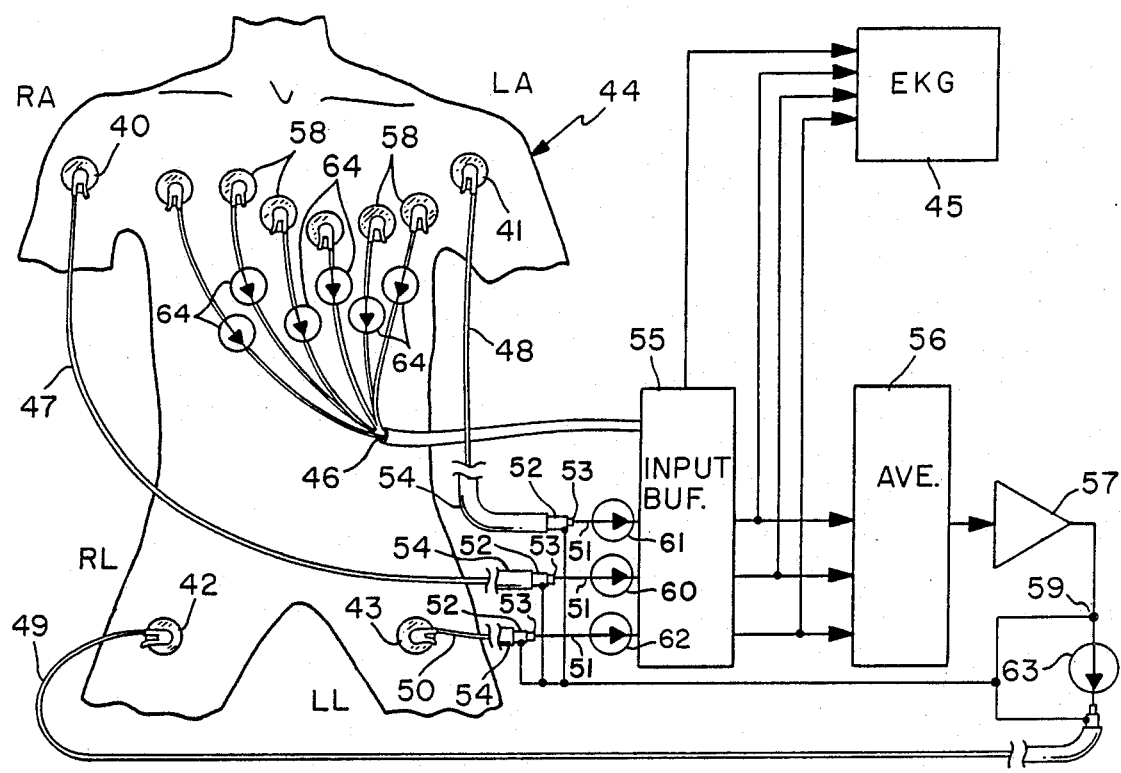
FIG. 4 is a diagam showing the negative feedback, noise cancellation system of this invention and its of connection to the human body.

FIG. 1 shows a basic connection orientation between a patient's body 10 and a standard EKG tracing or output module 11 utilizing a prior art negative feedback system. Four electrodes 12, 13, 14 and 15 of a design known in the art are shown connected to the patient body 10 at predetermined locations on or near the limbs and are thus referred to as "limb" electrodes. A plurality of electrodes 16, typically six (6), are shown placed at predetermined locations on the chest of the patient 10. The chest electrodes 16 receive cardiac signals or voltages and transmit them, via a cable set 25, to an input buffer 26. The signals are then transmitted to the EKG output module 11 for display and/or recording.

Each limb electrode 12, 13, 14 and 15 is shown communicatively linked to a cable 17, 18, 19 and 20, respectively. Referring also to FIG. 2, cables 17–20 have a conductive signal lead or wire 21 and a conductive shield 22. An inner layer of non-conductive insulation 23 is disposed to separate the inner lead 21 from contact with the shielding 22. In this configuration, the shield 22 isolates the lead 21 from outside electrical interference. Additionally, an outside layer of insulation 24 preferably surrounds the shield 22 to provide a unitary cable structure and for patient safety.

Limb electrodes 12, 13 and 15 are designated "monitoring" electrodes; they are placed at right arm (RA), left arm (LA), and left leg (LL) locations, respectively, to receive signals from the patient body 10. These signals are transmitted by the "monitoring" leads 21 to the input buffer or buffer amplifier 26. Alternatively, individual buffer amplifiers (not shown) may be connected to each lead 21. The input buffer 26 increases the input impedance for each input signal and, thus, reduces the effect of impedance variations in electrodes 12–16. The output signals from the input buffer 26 are then transmitted to the EKG output module 11 for display and/or recording. Limb electrode 14 is shown placed at a predetermined location on the right leg (RL) of the patient 10. Electrode 14, which is designated a "driver" electrode, is not utilized to receive bio-electric signals from the patient 10, but instead is used to transmit a voltage to the patient 10 as described below.

The signals detected at the monitoring electrodes 12, 13 and 15 are also transmitted from the input buffer 26 to a right leg driver circuit 27 known in the art. Typically, the right leg driver circuit 27 is housed with the input buffer 26 and the output module 11 to form a unitary EKG apparatus. The right leg driver circuit 27 comprises averaging circuitry 28 which processes the input signals to produce an average voltage. The average voltage is transmitted to a driver amplifier 29 which has a negative gain ranging from minus 10 to minus 100 and yields a feedback or correction voltage. The feedback voltage is transmitted to the right leg (RL) of he patient 10 via the driver electrode 14 to cancel body noise by forcing the body voltage toward zero volts.

The shield 22 of each cable 17-20 is shown to be connected to a patient side ground 30. The patient side ground 30 differs from a typical electrical ground in that it does not terminate at a conventional building ground, for example, via a wall socket. Rather, the patient side ground 30 is local to the system 27 circuitry and isolated from the building ground. The averaging circuitry 28 is also shown to be connected to the patient side ground 30.

As previously mentioned, prior art connection orientations such as that shown in FIG. 1, introduce time delays in the feedback voltage which may cause the system to oscillate. The primary source of delay is caused by the capacitance of the cables 17-20 which inherently results from their structural configuration. A capacitor is formed by each conductive lead 21 and shielding 22 which are separated by the dielectric inner insulation layer 23. This time delay source is difficult to remove without reducing the accuracy of measurement in the system because the shielding 22 is necessary to keep out interference from other devices present in a clinical environment.

The effect of cable capacitance on stability may be understood by reference to FIG. 3 which shows a schematic circuit representation of the prior art system connections of FIG. 1. The exemplary resistors and capacitors shown in the drawing are parasitic and unintentional. Four resistors R0, R1, R2 and R3, represent the resistance or impedance of the respective electrodes 12-15, combined with the resistance of the body tissue, the skin and the skin-electrode interface proximate each such electrode 12-15. Resistance R0 represents the combined resistance at the right leg or driving electrode 14. Resistances R1, R2 and R3 represent the combined resistance of each monitoring electrode 12, 13 and 15, respectively. Four capacitors C0, C1, C2 and C3 are shown connected to the patient side ground 30 of the circuitry. The capacitors C1, C2 and C3 each represent the individual capacitance that arises from the respective monitoring cables 17, 18 and 20 as discussed above. Similarly, capacitor C0 represents the capacitance that results from the right leg or driving cable 19. In this configuration, current output by the driver amplifier 29 flows from the right leg driver electrode 14 through the body 10 to the monitoring electrodes 12, 13, 15 and then through the monitoring cables 17, 18, and 20. Thus, the resistances R1, R2, and R3 precede the respective capacitances C1, C2, and C3.

An electrical circuit with a resistance preceding a capacitance yields a time delay because the capacitance needs to acquire a charge to follow a voltage while, at the same time, the resistance limits the amount of current that can flow to charge the capacitance. The time delay is equal to the product of the resistance and the capacitance. Typical values for a medical electrode connection are approximately 10 K ohms for the resistances (due primarily to electrode and body or current limiter resistance) and 200 pf for the capacitance arising from electrode cables. These exemplary values yield a time delay of approximately 2 microseconds. This delay is significant enough to cause appreciable oscillation and instability in the feedback and monitoring systems. As a result, the effectiveness of noise cancellation is reduced and the quality of signal analysis is diminished.

FIG. 3 further shows four current limiters, designated as L0, L1, L2 and L3, added to the feedback system of FIG. 1. The current limiters L0-L3 conduct low level signals, but cease to conduct or limit conduction when a voltage or current overload is sensed. Although, current limiters L0-L3 are highly desirable for patient safety reasons, they substantially increase the amount of resistance in the circuit. Accordingly, they increase the potential for time delay in the system and make stability even more difficult to achieve with desirable diagnostic sensitivity. The monitoring limb current limiters L1, L2 and L3 appear after the monitoring cable capacitances C1, C2 and C3, and hence do not create significant time delays in the monitoring cables 17, 18, and 20. However, the right leg current limiter L0 connected in the right leg cable 19 causes a significant time delay because it precedes the right leg cable capacitance C0 in the circuit. The right leg current limiter L0 also adds to the monitoring electrode resistances R1, R2 and R3 which interact with the monitoring cable capacitances C1, C2 and C3. The eventual effect of the right leg current limiter L0 (in series with the right leg electrode resistance R0 and each of the monitoring electrodes R1, R2 and R3, respectively) is a time delay in charging the uncompensated cable capacitances C1, C2 and C3. Thus, the current limiter L0 on the right leg cable 19 poses a significant time delay problem for the entire prior art feedback system.

FIG. 4 shows the bio-electric noise cancellation system of the present invention. The system is usable with an electro-medical diagnostic apparatus, such as an EKG apparatus, or with other bio-electric monitoring apparatus. Four limb electrodes 40, 41, 42 and 43 are shown connected directly to the patient body at predetermined locations on or near the limbs of the patient 44. A plurality of chest electrodes 58 are also shown placed at predetermined locations on the chest of the patient 44 to receive and transmit cardiac signals, via a cable set 46, to an EKG tracing or output module 45. Limb cables 47, 48, 49 and 50 extend from the respective limb electrodes 40-43, each cable 47-50 having a conductive lead 51, a conductive shield 52, an inner insulator 53, and an outer insulator 54.

Monitoring electrodes 40, 41 and 43 are shown placed at right arm (RA), left arm (LA), and left leg (LL) locations to receive voltage signals from the body 44. These signals are transmitted by the conductive monitoring leads or signal paths 51 of the cables 47, 48 and 50 to an input buffer 55. The voltage signals are then transmitted to the EKG output module 45 for recording and/or display. The limb electrode or driving electrode 42 is shown placed at a predetermined location on the right leg of the patient 44 to transmit a feedback or correction voltage into the body 44. Additional driving electrodes are usable at alternative locations on the body 44 consistent with this invention.

Current limiters 60, 61 and 62 are connected in-line with the monitoring electrodes 40, 41 and 43, preferably at the terminus of the monitoring cables 47, 48 and 50 at the input buffer 55. The current limiters are preferably medical current limiting circuits as described by Kroll in U.S. Pat. No. 4,744,369. Alternatively, a large series resistance may be used. The monitoring limb current limiters 60-62 limit current levels on the signal paths of the monitoring limb cables 47, 48, and 50 in the event of a device malfunction or patient contact with an outside current source. At normal current levels, bio-electric signals are conducted through the monitoring limb current limiters 60-62. As shown in this configuration, the resistance attributable to the current limiters 60-62 is preceded by the capacitance attributable to the monitoring cables 47, 48 and 50. A plurality of chest current limiters 64 are shown connected in-line with the chest electrodes 58 for patient safety purposes. Current limiter 63 is shown connected at the output of a driver amplifier 57, preferably at the connection of the terminal end of the right leg cable 49 thereto. In this configuration, the resistance attributable to the right leg current limiter 63 also precedes the capacitance of the right leg cable 49.

The signals received from the monitoring electrodes 40, 41 and 43 are also transmitted to averaging circuitry 56 which processes them to produce an average voltage signal. The averaging circuitry 56 is a summing network or a similar system as known in the art. The average voltage is transmitted to the driver amplifier 57 which has a large negative gain in the range of 1,000. The driver amplifier 57 has an output which varies as a function of the noise level on the body 44, as determined from the average of the voltages of the monitoring electrodes 40, 41 and 43. The amplifier 57 output provides the feedback or correction voltage which is transmitted to the right leg electrode 42 via the right leg cable 49. The feedback voltage compensates for the common-mode voltage on the body 44 and forces the average patient voltage to assume a value near zero volts with respect to the patient side ground. The feedback system of this invention increases the common-mode rejection ratio of the overall EKG system and reduces noise and interference.

In the present invention, the shields 52 of the four limb cables 47–50 are not connected to a patient side ground or other connection scheme as known in the prior art. Rather, all four cable shields 52 are preferably connected to the output of the driver amplifier 57. Importantly, the shield 52 of the right leg cable 49 is conductively connected to the output of the driver amplifier 57 at a point in the circuit before the right leg current limiter 63, for example, at a node or point 59, as shown in FIG. 4. The shields 52 of the monitoring limb cables 47, 48, and 50 are also preferably connected at the node 59 although they may be connected at other points in the circuit prior to the right leg current limiter 63; for example, at the respective outputs of the buffer amplifier 55 or to the output averaging circuitry 56. The physical conductive connection of the shields as described and shown in the drawings may be made utilizing means known in the art. For example, connectors, printed circuit boards and lead means can be constructed and arranged to provide the communicative link to practice the teachings of this invention.

Referring to FIGS. 5–8, the embodiments of the present invention are shown in consolidated schematic diagrams of the circuit elements previously described with respect to FIG. 4. Since the three monitoring signal paths from the RA, LA and LL limb locations are substantially equivalent in terms of their bio-electric signal reception function, they are consolidated into one parallel combination of equivalent electrode resistance RX and equivalent cable capacitance CX. Again, these representations are parasitic and are shown for purposes of discussion. Since the right leg current limiter 63 exerts the predominant influence on time delay and thus stability, its effect on the system is the focus of analysis. The resistance and capacitance attributable to the right leg electrode 42 and right leg cable 49 are shown as R0 and C0, respectively. The monitoring lead current limiters 60, 61 and 62 are not shown because of their relatively limited influence with respect to system stability. However, the present invention also alleviates the prior art problem of uncompensated capacitance to which the omitted current limiters 60–62 contribute. Voltage (VI) represents the instantaneous voltage at any given lead 51 of the monitoring cables 47, 48, or 50. Voltage (VO) represents the instantaneous voltage at the output of the driver amplifier 57.

Figure 5:
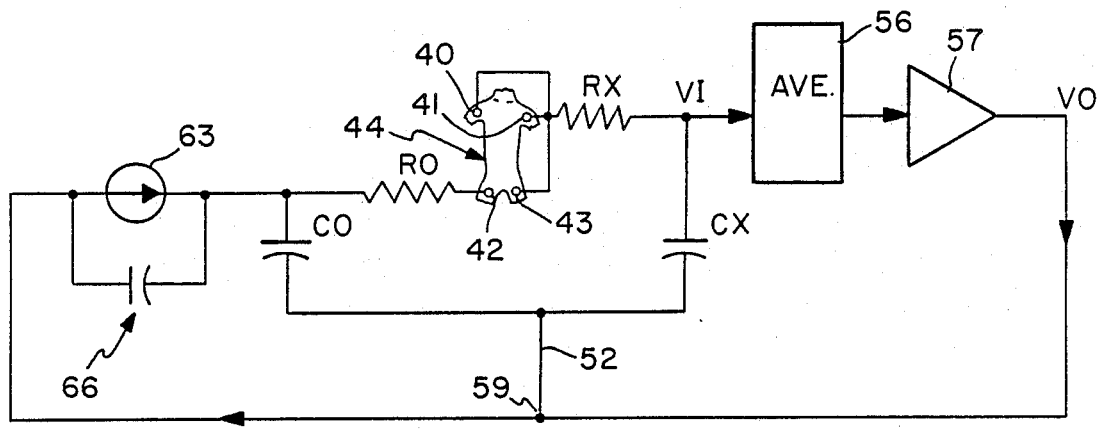
FIG. 5 is a schematic circuit representation of the system shown in FIG. 4.

FIG. 5 shows an equivalent schematic of the connection of all of the cable shields 52 to the output of the driver amplifier 57 and at a point in the circuit before the right leg current limiter 63. Thus, the right leg cable capacitance C0 does not need to be charged through the resistance R0 of right leg current limiter 63 since both sides of the capacitance C0 are connected to the equivalent voltage VO of the driver amplifier 57 output. Similarly, the monitoring cable capacitance CX does not charge through resistances RO and RX (as well as the resistance attributable to the right leg current limiter 63) since both sides of the monitoring cable capacitance CX will eventually be at the same voltage VO. The effect of the specific conductive link between the amplifier 57 output to the shields 52 is to drive the cable capacitances CO and CX as a function of feedback signal transmitted through the leads 51. This eliminates the problem of having the cable capacitances CO and CX charge through a resistance, and thus reduces time delays in the feedback system.

FIG. 5 further shows a first capacitor 66 which is connected in parallel with the right leg current limiter 63. The capacitor 66 provides a shunt which allows high frequency feedback signals to bypass the right leg current limiter 63. These high frequency signals are particularly useful for maintaining loop stability and are less important for patient safety. Therefore, the capacitor 66 shunt enhances signal sensitivity. Further, the capacitor 66 shunt does not present a danger to the patient 44 because potentially harmful low frequency signals are unable to pass through it.

Figure 6:
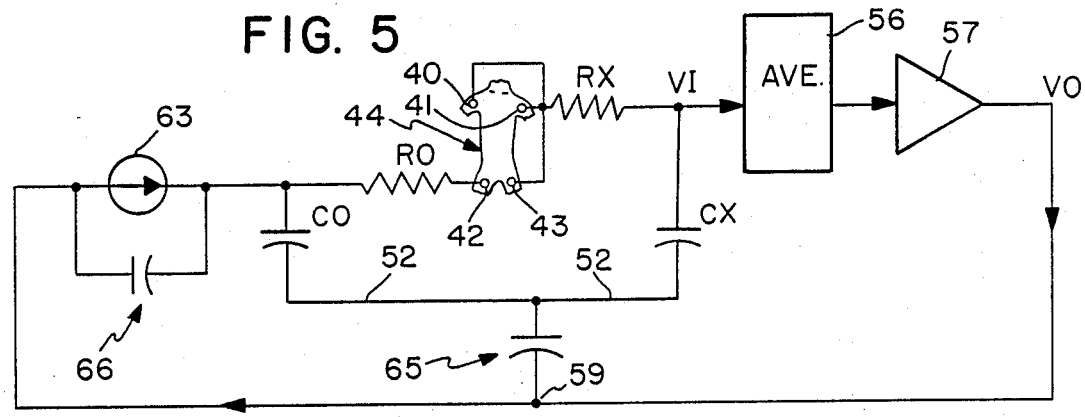
FIGS. 6-8 are schematic circuit diagrams of other embodiments of the negative feedback noise cancellation system of this invention.

FIG. 6 shows another circuit embodiment of the invention. In this configuration, the connection between the driver amplifier 57 output and the cable shields 52 is not direct, but rather runs through a second or blocking capacitor 65. The addition of the capacitor 65 yields a slight increase in time delay of the feedback, but lowers leakage current through the cable shields 52. The blocking capacitor 65 thus denies a DC or low frequency leakage path should a cable shield 52 come in contact with the patient body surface 44.

Figure 7:
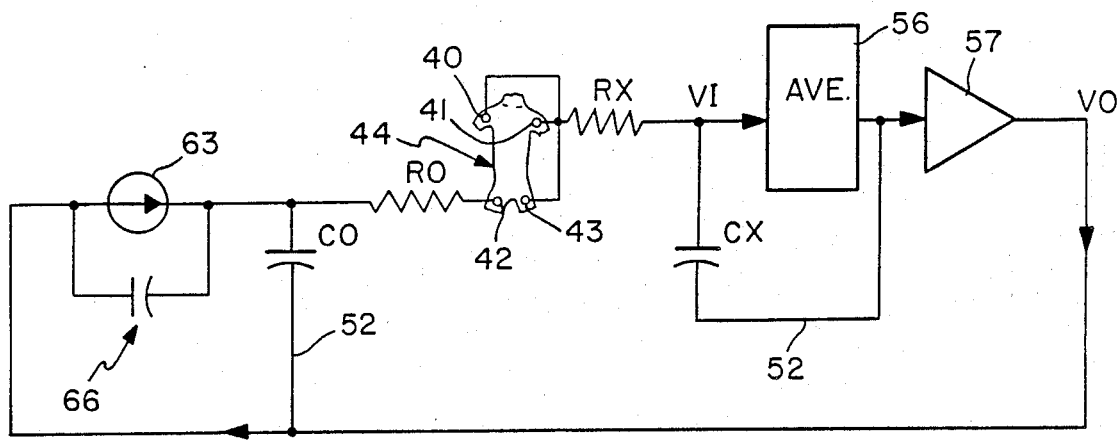
Figure 8:
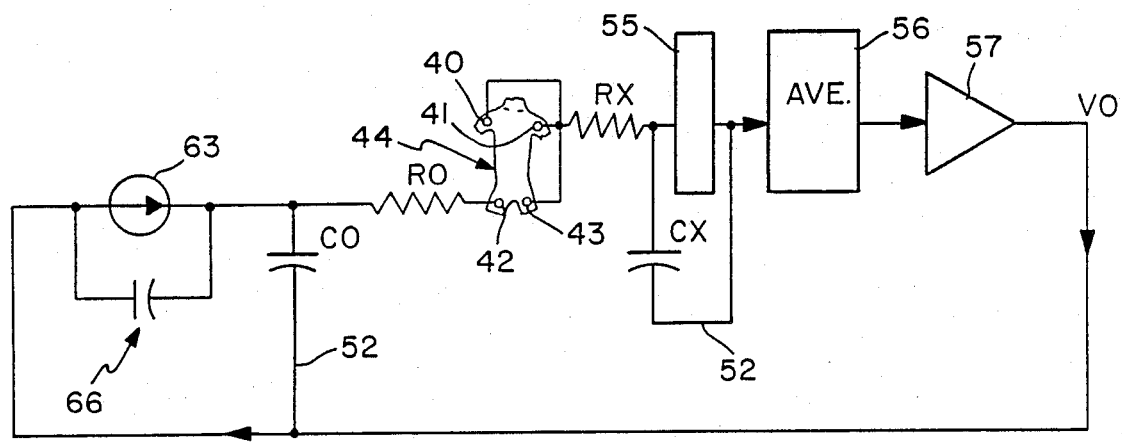

FIG. 7 shows another embodiment of the system wherein the shields 52 of the monitoring cables 47, 48 and 50 are communicatively connected to and driven by the output of the averaging circuitry 56. FIG. 8 shows an embodiment of the system wherein the shields 52 of the monitoring cables 47, 48 and 50 are communicatively connected to and driven by the respective outputs of the input buffer 55.

The device of the bio-electric noise cancellation system significantly reduces the time delay in providing a feedback voltage to the patient body 44. This permits the driver amplifier 57 to be run at very large gains in the range of 1,000. The resultant high gain of the driver amplifier 57 significantly decreases noise on the body 44 as the feedback voltage compensates the common mode voltage. Improvements of approximately 1:3000 or 30 dB in the noise level power reduction at 60 Hz have been realized utilizing the bio-electric noise cancellation system of this invention.

The method of the bio-electric noise cancellation system reduces feedback delay in a medical, negative feedback system. The method comprises the steps of obtaining bio-electric signals from a plurality of locations on the patient body 44 and transmitting the bio-electric signals via shielded leads or conductors 51. The bio-electric signals are averaged to provide an average signal which is amplified by a predetermined large, negative factor to provide a correction or feedback signal. The correction signal is driven or provided, also via a shielded lead 51, to the patient body 44. Finally, a conductive link is established between the shield 52 of the driving lead 51 and the correction signal.

As many changes are possible to the embodiments of this invention, utilizing the teachings thereof, the description above and the accompanying drawings should be viewed in the illustrative and not in the limited sense.

That which is claimed is:

1. A system for cancelling bio-electric noise on a human body, comprising:
   (a) a plurality of monitoring electrodes for reception of bio-electric signals, each said monitoring electrode having a conductive monitoring lead and a monitoring shield around said monitoring lead;
   (b) at least one driving electrode for transmission of a noise cancelling correction voltage, said at least one driving electrode having a conductive driving lead and a driving shield around said driving lead;
   (c) signal averaging means having an input and an output, said monitoring leads being connected to said signal averaging means input;
   (d) an amplifier providing said correction voltage and being connected to said signal averaging means output, said amplifier having an output connected to said at least one driving lead; and
   (e) a conductive connection between said at least one driving shield and said amplifier output.

2. The bio-electric noise cancelling system of claim 1, further comprising a conductive connection between said monitoring shields and said amplifier output.

3. The bio-electric noise cancelling system of claim 2, further comprising a conductive connection between said monitoring shields and said signal averaging means output.

4. The bio-electric noise cancelling system of claim 1, further comprising a buffer amplifier having an input and an output, said monitoring leads being connected to said buffer amplifier input and said buffer amplifier output being connected to said signal averaging means input.

5. The bio-electric noise cancelling system of claim 4, further comprising a conductive connection between said monitoring shields and said buffer amplifier output.

6. The bio-electric noise cancelling system of claim 1, further comprising current limiting means connected between said amplifier output and said driving lead, and wherein said driving shield is further connected between said amplifier output and said current limiting means.

7. The bio-electric noise cancelling system of claim 6, further comprising a conductive connection between said monitoring shields and said amplifier output between said amplifier output and said current limiting means.

8. The bio-electric noise cancelling system of claim 6, further comprising a first capacitor means connected between said amplifier output and said driving lead, in parallel with said current limiting means.

9. The bio-electric noise cancelling system of claim 1, further comprising a capacitor means connected in series with said conductive connection between said amplifier output and said at least one driving shield.

10. The bio-electric noise cancelling system of claim 8, further comprising second capacitor means connected between said amplifier output and said conductive connections to said driving and monitoring shields.

11. The bio-electric noise cancelling system of claim 7, wherein said driving shield and said monitoring shields are connected between said amplifier output and said current limiting means at a single node, said system further comprising a second capacitor connected in series between said amplifier output and said node.

12. The bio-electric noise cancelling system of claim 1, wherein said amplifier has a large negative gain of at least 50.

13. The bio-electric noise cancelling system of claim 1, further comprising current limiting means connected between said monitoring electrodes and said signal averaging means.

14. The bio-electric noise cancelling system of claim 1, wherein said monitoring electrodes comprise three limb electrodes for placement proximate the right arm, left arm and left leg positions of the body, respectively, and six chest electrodes adapted to fit a predetermined configuration on the precordial region of the patient, and wherein a single said driving electrode is for placement proximate the right leg of the body.

15. A negative feedback, noise cancelling system for use with a medical diagnostic apparatus to monitor a patient, comprising:
   (a) a plurality of monitoring electrodes for reception of bio-electric signals from the patient, each said monitoring electrode having a conductive lead and a conductive shield coextensive with and spacially surrounding each said monitoring electrode lead;
   (b) a driving electrode for transmission of a noise cancelling correction voltage to the patient, said driving electrode having a conductive lead and a conductive shield coextensive with and spacially surrounding said driving electrode lead;
   (c) signal averaging means receiving signals from said monitoring electrodes to provide an output average signal;
   (d) a driver amplifier having an input and an output, said driver amplifier input connected to said signal averaging means and being for reception of said output average signal and for provision of said correction voltage, said driver amplifier output being connected to said driving electrode lead; and
   (e) a conductive connection between said driver amplifier output and said coextensive shields around said driving electrode and monitoring electrode leads.

16. The noise cancelling system of claim 15, further comprising a current limiter connected between said driver amplifier output and said driving electrode lead, said driving electrode shield and said monitoring electrode shields further being connected between said driver amplifier output and said current limiter.

17. The noise cancelling system of claim 16, further comprising first and second capacitors, said first capacitor being connected between said driver amplifier output and said driving electrode lead, in parallel with said current limiter, and said second capacitor being connected in series between said driver amplifier output and said conductive connections to said driving electrode and monitoring electrode shields.

18. A negative feedback, right leg driver system for use with a medical diagnostic apparatus to cancel noise voltages on a patient, comprising:
   (a) a plurality of electrodes for connection to the patient at predetermined locations, said electrodes including three monitoring electrodes for reception of voltage signals from the patient, and a driving electrode for transmission of a noise cancelling correction voltage to the patient;

(a) a plurality of conductive leads having conductive shields around said leads, each said lead being connected to one of said electrodes;
(c) a signal averager having an input connected to said monitoring electrode leads to receive signals therefrom, said signal averager further having an output providing an average voltage signal;
(d) a driver amplifier connected to said signal averager output, said driver amplifier having an output providing said correction voltage to said driving electrode lead, said correction voltage being a large negative multiple of said average voltage signal;
(e) a current limiter having an input side and an output side, said current limiter being connected between said driver amplifier output and said driving electrode lead; and
(f) a conductive link connected to each said shield, said conductive link further being connected between said driver amplifier output and said current limiter, said conductive link conducting said correction voltage between said driver amplifier output and said shields, whereby said input and output sides of said current limiter have an equivalent potential which is equal to said correction voltage.

19. A medical right leg driver system of the type having a plurality of electrodes for connection to a patient's body including a plurality of monitoring electrodes having shielded leads, and one driving electrode having a shielded lead, signal averaging means communicatively linked to the monitoring electrode leads, a driver amplifier connected to the signal averaging means and having an output, said driver amplifier output being connected to the driving electrode via the driving electrode lead, and current limiting means being connected to the driver amplifier output, wherein the improvement comprises a conductive connection of the shield around the driving electrode lead between the driver amplifier output and the current limiting means.

20. A method of reducing feedback delay in a medical, negative feedback system, comprising the steps of:
(a) obtaining bio-electric signals from a plurality of locations on a patient body and transmitting said bio-electric signals via shielded conductive leads;
(b) averaging said bio-electric signals to provide an average signal;
(c) amplifying said average signal by a large, negative factor to provide a correction signal;
(d) providing said correction signal to the patient body via a shielded driving lead; and
(e) establishing a conductive link between said driving lead shield and said correction signal.

* * * * *